United States Patent [19]

Arndt et al.

[11] 4,441,915
[45] Apr. 10, 1984

[54] DIURETHANES AND HERBICIDAL COMPOSITIONS CONTAINING THE SAME

[75] Inventors: Friedrich Arndt; Gerhard Boroschewski, both of Berlin, Fed. Rep. of Germany

[73] Assignee: Schering Aktiengesellschaft, Berlin and Bergkamen, Fed. Rep. of Germany

[21] Appl. No.: 283,661

[22] Filed: Jul. 15, 1981

Related U.S. Application Data

[63] Continuation of Ser. No. 101,051, Dec. 6, 1979, which is a continuation of Ser. No. 925,552, Jul. 17, 1978.

[30] Foreign Application Priority Data

Jul. 18, 1977 [DE] Fed. Rep. of Germany ....... 2732848

[51] Int. Cl.³ .................... A01N 37/44; C07C 149/43; C07C 125/073; C07C 125/075
[52] U.S. Cl. ........................................ 71/100; 560/16; 560/29; 71/111
[58] Field of Search ...................... 560/29, 16; 71/111, 71/118, 100

[56] References Cited

U.S. PATENT DOCUMENTS 3,133,808  5/1964  Hamm ..................................... 71/118
3,404,975  10/1968 Wilson et al. ........................... 71/111
3,551,477  12/1970 Koenig et al. .......................... 71/111
3,692,820  9/1972  Boroschewski et al. ............. 71/111
3,865,867  2/1975  Olin et al. .............................. 71/118
3,901,936  8/1975  Boroschewski et al. ............. 71/111
3,904,669  9/1975  Boroschewski et al. ............. 71/111
3,920,727  11/1975 Metzger et al. ........................ 71/111
3,997,325  12/1976 Cross et al. ............................ 71/111
4,022,611  5/1977  Vogel et al. ............................ 71/118
4,090,865  5/1978  Baker ..................................... 71/118

FOREIGN PATENT DOCUMENTS 1475241  2/1967  France ................................... 560/29

OTHER PUBLICATIONS

Koenig et al., "Herbicidal Dicarbamtes", Chem. Abs., vol. 77 (1972), 34175v.

Primary Examiner—Bernard Helfin
Attorney, Agent, or Firm—Michael J. Striker

[57] ABSTRACT

A composition containing at least one compound of the formula

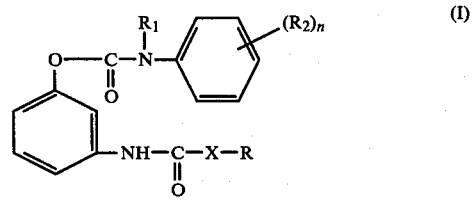

in which
R is alkyl, alkenyl, alkinyl, halogenoalkyl or alkoxyalkyl,
$R_1$ is alkoxyalkyl or dialkoxyalkyl,
$R_2$ is alkyl or alkoxy, and
x is oxygen or sulfur and
n is 0, 1, 2 or 3.

The compounds have a strong herbicidal effect against various weeds together with a broad selectivity in regard to agricultural plants, particularly potatoes, cotton, peanuts, carrots and rice.

4 Claims, No Drawings

DIURETHANES AND HERBICIDAL COMPOSITIONS CONTAINING THE SAME

This is a continuation, of application Ser. No. 101,051, filed Dec. 6, 1979 which in turn is a continuation of Ser. No. 925 552, filed July 17, 1978.

BACKGROUND OF THE INVENTION

The invention relates to diurethanes, herbicidal compositions containing the same and a process for making same.

Diurethanes have already been used in the prior art for suppression of weeds such as for instance 3-methylcarbanilic acid-[3-(methoxycarbonylamino)-phenyl]-ester and the carbanilic acid-(3-(ethoxycarbonylamino)-phenyl)ester (West German Pat. No. 1,567,151).

These agents have a comparatively narrow spectrum of activity, though they have a superior selectivity when used in beta-beet cultures.

It is an object of the present invention to provide for an agent which has a broader spectrum of activity and is particularly selective towards potatoes, cotton, peanuts, carrots and rice.

SUMMARY OF THE INVENTION

This object is solved by a composition which contains at least one compound of the formula

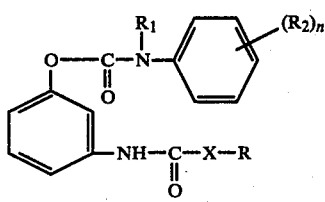

in which
R is alkyl, alkenyl, alkinyl, halogenoalkyl or alkoxyalkyl,
$R_1$ is alkoxyalkyl or dialkoxyalkyl,
$R_2$ is alkyl or alkoxy,
X is oxygen or sulfur, and
n is 0, 1, 2 or 3.

The compounds are active against many undesirable plant families such as Digitalis, Valerianella, Trifolium, Portulaca, Papaver, Kochia, Solanum, Escholtzia, Euphorbia, Brassica, Datura, Ipomea, Setaria, Agrostis, Alopecurus, Bromus, Echinochloa, Digitaria.

The amounts used for the selective weed suppression are about 0.5 to 5 kg of active agent per 2.5 acres.

The diurethanes of the invention surprisingly and contrary to the prior art compounds of an analogous constitution can be used also in non-best cultures, for instance in cultures involving potatoes, cotton, peanuts, carrots, rice and others without causing any damage. This, of course, is of substantial economic importance.

Among the diurethanes of the invention those are superior in regard to herbicidal and selective activity in which in the above formula I, R is $C_1$–$C_4$-alkyl, $C_2$–$C_4$-alkenyl, $C_3$–$C_4$-alkinyl, halogen-$C_1$–$C_4$-alkyl or $C_1$–$C_4$-alkoxy-$C_1$–$C_4$-alkyl and $R_1$ is $C_1$–$C_4$-alkoxy-$C_1$–$C_4$-alkyl or di-$C_1$–$C_4$-alkoxy-$C_1$–$C_4$-alkyl, and $R_2$ is $C_1$–$C_3$-alkyl or $C_1$–$C_3$-alkoxy.

The diurethanes of the invention can either be used singly or intermixed with each other or in mixture with other active agents. Depending on the particular purpose there are for instance the following herbicidal agents which, if desired, can be added immediately prior to application of the compounds of the invention:
substituted anilines,
substituted aryloxycarbonylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzoxazinones,
substituted benzthiazoles,
substituted benzthiadiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates,
substituted quinazolines,
substituted cycloalkylamidocarbonylthiol acids and their salts, esters and amides,
substituted cycloalkylcarboxylamido-thiazoles,
substituted dicarboxylic acids and their salts, esters and amides,
substituted dihydrobenzofuranylsulfonates,
substituted disulfides,
substituted dipyridylium salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidinediones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, ester and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyridazones, substituted pyridine-carboxylic acids and their salts, esters and amides,
substituted pyridines,
substituted pyridinecarboxylates,
substituted pyridinones,
substituted pyrimidones,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazolediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urothidindiones.

In addition, other additives can also be used, for instance, non-phytotoxic additives which result in a synergistic increase of activity in herbicides, like wetting agents, emulsifiers, solvents and oily additives.

It is preferred to use the compounds of the inventions or mixtures thereof in the form of compositions such as powders, dusting agents, granulates, solutions, emulsions or suspensions. Liquid and/or solid carrier materials or diluents should be added and, if desired, wetting agents, adhesion promoting agents, emulsifiers, and/or dispersants can also be added.

Suitable liquid carrier materials are, for instance, water, aliphatic and aromatic hydrocarbons, such as, benzene, toluene, xylene, cyclohexanone, isophorone, dimethylsulfoxide, dimethylformamide, and furthermore, mineral oil fractions.

As solid carrier materials there are suitable mineral earths, for instance, tonsil, silicagel, talc, kaolin, attaclay, limestone, silicic acid, and plant products, such as for instance flours.

They may also be added surface active agents as for instance calciumlignosulfonate, polyoxyethylenealkylphenylether, naphthalenesulfonic acids and their salts, phenolsulfonic acids and their salts, formaldehyde condensation products, fatty alcohol sulfates, and substituted benzolsulfonic acids and their salts.

The amounts of the agent or agents of the invention and the different compositions can be varied within wide limits. The compositions may for instance contain about 10 to 80% by weight of active agents, about 90 to 20% by weight of liquid or solid carrier materials and up to 20 weight percent of surface active agents in which case a corresponding reduction of the carrier materials would take place.

The application of the compounds can be effected in conventional form, for instance with water as carrier materials in spray amounts of about 100 to 1000 liters per about 2.5 acres. The application of the compounds is possible by the so-called "low volume" and "ultra low volume" method and in the form of so-called microgranulates.

PROCESS OF MAKING THE COMPOUNDS

The diurethanes of above formula I can be made by different processes.

I. Compounds of the formula

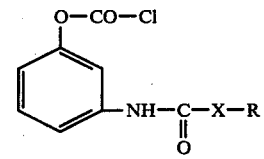

can be reacted with amines of the formula

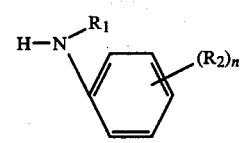

in the presence of an acid acceptor, for instance by adding an excess of the amine or an inorganic base, like sodium hydroxide, sodium carbonate, or potassium carbonate, or by adding a tertiary organic base such as triethylamine.

II. Compounds of the formula

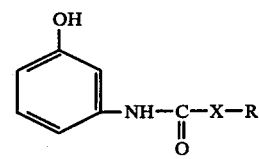

can also be reacted with carbamoylchlorides of the formula

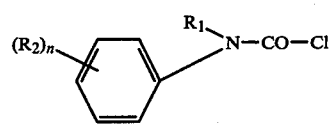

at temperature of 0° to 100° C. in the presence of a tertiary organic base such as triethylamine or pyridine or also as alkali salts, for instance, as sodium or potassium salts, and the compounds may be dissolved in a solvent such as methylisobutylketone or aceticethylester.

III. Compounds of the formula

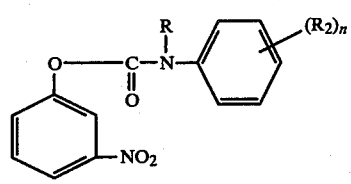

may also be hydrogenated in the presence of a catalyst, for instance nickel in a solvent like methanol to form the corresponding amine. The latter product is then reacted with compounds of the formula

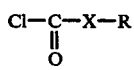  VII to form the desired products of the invention. This reaction is also carried out in the presence of an acid acceptor, for instance an inorganic base, like sodium hydroxide, sodium carbonate or potassium carbonate, or in the presence of a tertiary organic base, for instance triethylamine, and the reactants are dissolved in a solvent, for instance, acetic ethylester.

The products obtained in all cases are then isolated in conventional manner. In all of the processes just described R, $R_1$, $R_2$, X and n have the same meaning as in above formula I.

PREFERRED EMBODIMENTS OF THE INVENTION

The following examples will illustrate the making of the compounds of the invention.

EXAMPLE 1

N-(2,2-dimethoxyethyl)-3-methylcarbanilic acid-[3-(methoxycarbonylamino)-phenyl]-ester (Compound No. 1)

A solution of 26 g (0.1 mol) of chloroformic acid-3-methoxycarbonylamino-phenylester is added dropwise with a solution of 13.8 g of potassium carbonate in 50 ml water to a solution of 19.5 g (0.1 mol) of N-(2,2-dimethoxyethyl)-3-toluidene in 50 ml acetic ethylester while stirring and cooling the mixture to 10° to 15° C. The mass is then further subjected to stirring for another 30 minutes at 15° C. The organic phase is then separated, is diluted with 100 ml of acetic ester and is washed at 0° C. with a small amount of dilute sodium hydroxide, dilute hydrochloric acid and water.

After drying on magnesium sulfate the mass is concentrated in a partial vacuum. After adding isopropyl ether the reaction products are subjected to crystallization. The yield is 23.6 g=61% of the calculated value; m.p. 70° to 72° C.

In an analogous manner the following diurethanes were produced:

| Compound No. | Name of Compound | Physical constants |
|---|---|---|
| 2. | N—(2-methoxyethyl)-carbanilic acid-(3-(methoxycarbonylamino)-phenyl-ester | m.p.: 116–118° C. |
| 3. | N—(2,2-dimethoxyethyl)-carbanilic acid-(3-(methoxycarbonylamino)-phenyl)-ester | m.p.: 115–117° C. |
| 4. | N—(2-methoxyethyl)-3-methylcarbanilic acid-(3-(methoxycarbonylamino)-phenyl)-ester | m.p.: 86–89° C. |
| 5. | N—(2-methoxyethyl)-carbanilic acid-(3-(ethoxycarbonylamino)-phenyl)-ester | m.p.: 70–71° C. |
| 6. | N—(2,2-dimethoxyethyl)-carbanilic acid-(3-isopropoxycarbonylamino)-phenyl)-ester | m.p.: 85–87° C. |
| 7. | N—(2-methoxyethyl)-carbanilic acid-(3-(isopropoxycarbonylamino)-phenyl)-ester | m.p.: 65–67° C. |
| 8. | N—(2-methoxyethyl)-carbanilic acid-(3-(sec.-butoxycarbonylamino)-phenyl)-ester | $n_D^{20}$: 1.5131 |
| 9. | N—(2,2-dimethoxyethyl)-carbanilic acid-(3-(isobutylcarbonylamino)-phenyl)-ester | m.p.: 94–95° C. |
| 10. | N—(2-methoxyethyl)-carbanilic acid-(3-(2-methylpropoxycarbonylamino)-phenyl)-ester | m.p.: 72–74° C. |
| 11. | N—(2-methoxyethyl)-carbanilic acid-(3-(allyloxycarbonylamino)-phenyl)-ester | $n_D^{20}$: 1.5398 |
| 12. | N—(2,2-dimethoxyethyl)-carbanilic acid-(3-(allyloxycarbonylamino)-phenyl)-ester | m.p.: 76–78° C. |
| 13. | N—(2,2-dimethoxyethyl)-carbanilic acid-(3-(2-propinyloxycarbonylamino)-phenyl)-ester | m.p.: 122° C. |
| 14. | N—(2-methoxyethyl)-carbanilic acid-(3-(2-propinyloxycarbonylamino)-phenyl)-ester | $n_D^{20}$: 1.5448 |
| 15. | N—(2,2-dimethoxyethyl)-carbanilic acid-(3-(methylthiocarbonylamino)-phenyl)-ester | m.p.: 100–102° C. |
| 16. | N—(2,2-dimethoxyethyl)-carbanilic acid-(3-(ethylthiocarbonylamino)-phenyl)-ester | m.p.: 85–87° C. |
| 17. | N—(2-methoxyethyl)-carbanilic acid-(3-ethylthiocarbonylamino)-phenyl)-ester | m.p.: 88–89° C. |
| 18. | N—(2-ethoxyethyl)-carbanilic acid-(3-methoxycarbonylamino)-phenyl)-ester | m.p.: 116–117° C. |
| 19. | N—(2-ethoxyethyl)-3-methylcarbanilic acid-(3-(methoxycarbonylamino)-phenyl)-ester | m.p.: 78–79° C. |
| 20. | N—(2,2-dimethoxyethyl)-3-methyl-carbanilic acid-(3-(methoxycarbonylamino)-phenyl)-ester | m.p.: 70–72° C. |
| 21. | N—(2,2-dimethoxyethyl)-4-methyl-carbanilic acid-(3-(methoxycarbonylamino)-phenyl)-ester | $n_D^{20}$: 1.7071 |
| 22. | N—(2-methoxyethyl)-3-methyl-carbanilic acid-(3-(ethoxycarbonylamino)-phenyl)-ester | $n_D^{20}$: 1.5559 |
| 23. | N—(2-ethoxyethyl)-carbanilic acid-(3-(ethoxycarbonylamino)-phenyl)-ester | m.p.: 48–50° C. |
| 24. | N—(2,2-dimethoxyethyl)-3-methyl-carbanilic acid-(3-(ethoxycarbonylamino)-phenyl)-ester | m.p.: 75–78° C. |
| 25. | N—(2-ethoxyethyl)-3-methylcarbanilic acid-(3-ethoxycarbonylamino)-phenyl)-ester | m.p.: 83–84° C. |
| 26. | N—(2,2-dimethoxyethyl)-4-methyl-carbanilic acid-(3-ethoxycarbonylamino)-phenyl)-ester | m.p.: 88–89° C. |
| 27. | N—(2,2-dimethoxyethyl)-4-methyl-carbanilic acid-(3-isopropoxycarbonylamino)-phenyl)-ester | m.p.: 87–88° C. |
| 28. | N—(2,2-dimethoxyethyl)-3-methyl-carbanilic acid-(3-(1-methylethoxy-carbonylamino)-phenyl)-ester | m.p.: 96° C. |
| 29. | N—(2,2-dimethoxyethyl)-4-methylcarbanilic acid-(3-butoxycarbonylamino)-phenyl)-ester | m.p.: 68° C. |
| 30. | N—(2,2-dimethoxyethyl)-3-methylcarbanilic acid-(3-(2-methylpropoxy-carbonylamino)-phenyl)-ester | m.p.: 112–113° C. |
| 31. | N—(2,2-dimethoxyethyl)-3-methyl-carbanilic acid-(3-(1-methylpropoxy-carbonylamino)-phenyl)-ester | m.p.: 94–95° C. |
| 32. | N—(2,2-dimethoxyethyl)-4-methylcarbanilic acid-(3-(2-methylpropoxycarbonylamino)-phenyl)-ester | m.p.: 103° C. |
| 33. | N—(2,2-dimethoxyethyl)-3-methylcarbanilic acid-(3-(2-methoxyethoxycarbonylamino)-phenyl)-ester | m.p.: 78–80° C. |
| 34. | N—(2,2-dimethoxyethyl)-3-methylcarbanilic acid-(3-allyloxycarbonylamino)-phenyl)-ester | m.p.: 78–80° C. |
| 35. | N—(2,2-dimethoxyethyl)-3-methylcarbanilic acid-(3-(2-propinyloxycarbonylamino)-phenyl)-ester | m.p.: 103–106° C. |

| Compound No. | Name of Compound | Physical constants |
|---|---|---|
| 36. | N—(2,2-dimethoxyethyl)-4-methylcarbanilic acid-(3-(2-propinyloxycarbonylamino)-phenyl)-ester | m.p.: 89–90° C. |
| 37. | N—(2-methoxyethyl)-carbanilic acid-(3-(3-methylthiocarbonylamino)-phenyl)-ester | m.p.: 98–100° C. |
| 38. | N—(2,2-dimethoxyethyl)-4-methylcarbanilic acid-(3-(methylthio-carbonylamino)-phenyl)-ester | m.p.: 79–80° C. |
| 39. | N—(2,2-dimethoxyethyl)-3-methylcarbanilic acid-(3-methylthiocarbonylamino)-phenyl)-ester | m.p.: 107° C. |
| 40. | N—(2,2-dimethoxyethyl)-3-methylcarbanilic acid-(3-(ethylthiocarbonylamino)-phenyl)-ester | m.p.: 79–82° C. |
| 41. | N—(2,2-dimethoxyethyl)-4-methylcarbanilic acid-(3-(ethylthiocarbonylamino)-phenyl)-ester | m.p.: 81° C. |
| 42. | N—(2,2-dimethoxyethyl)-carbanilic acid-(3-(ethoxycarbonylamino)-phenyl-ester | m.p.: 70–73° C. |
| 43. | N—(2,2-dimethoxyethyl)-carbanilic acid-(3-(sec.-butoxycarbonylamino)-phenyl)-ester | m.p.: 80–82° C. |
| 44. | N—(2-methoxyethyl)-4-methylcarbanilic acid-(3-(ethoxycarbonylamino)-phenyl)-ester | m.p.: 78° C. |
| 45. | N—(2-ethoxyethyl)-2-methylcarbanilic acid-(3-ethoxycarbonylamino)-phenyl-ester | m.p.: 65–68° C. |
| 46. | N—(2-methoxyethyl)-4-methylcarbanilic acid-(3-(methoxycarbonylamino)-phenyl)-ester | m.p.: 89–90° C. |
| 47. | N—(2-ethoxyethyl)-2-methylcarbanilic acid-(3-(methoxycarbonylamino)-phenyl)-ester | m.p.: 118–120° C. |
| 48. | 3-methyl-N—(2-propoxyethyl)-carbanilic acid-(3-(ethoxycarbonylamino)-phenyl)-ester | m.p.: 67–69° C. |
| 49. | 2-methyl-N—(2-propoxyethyl)-carbanilic acid-(3-(methoxycarbonylamino)-phenyl)-ester | m.p.: 76–78° C. |
| 50. | N—(2,2-dimethoxyethyl)-2-methylcarbanilic acid-(3-(2-propinyloxycarbonylamino)-phenyl)-ester | m.p.: 105–107° C. |
| 51. | N—(2,2-dimethoxyethyl)-4-methylcarbanilic acid-(3-(1-methylpropoxycarbonylamino)-phenyl)-ester | $n_D^{20}$: 1.7679 |
| 52. | N—(2-methoxyethyl)-4-methoxycarbanilic acid-(3-(methoxycarbonylamino)-phenyl)-ester | m.p.: 93–94° C. |
| 53. | N—(2-ethoxyethyl)-4-methylcarbanilic acid-(3-(methoxycarbonylamino)-phenyl)-ester | m.p.: 102–103° C. |
| 54. | N—(2-ethoxyethyl)-4-methylcarbanilic acid-(3-(ethoxycarbonylamino)-phenyl)-ester | m.p.: 68–70° C. |
| 55. | N—(2,2-dimethoxyethyl)-4-methylcarbanilic acid-(3-(allyloxycarbonylamino)-phenyl)-ester | $n_D^{20}$: 1.5145 |
| 56. | N—(2-butoxyethyl)-4-methylcarbanilic acid-(3-(ethoxycarbonylamino)-phenyl)-ester | $n_D^{20}$: 1.5391 |
| 57. | 4-methoxy-N—(2-methoxyethyl)-carbanilic acid-(3-(ethoxycarbonylamino)-phenyl)-ester | $n_D^{20}$: 1.5520 |
| 58. | N—(2-propoxyethyl)-carbanilic acid-(3-(methoxycarbonylamino)-phenyl)-ester | $n_D^{20}$: 1.5441 |
| 59. | 2-methyl-N—(2-methoxyethyl)-carbanilic acid-(3-(methoxycarbonylamino)-phenyl)-ester | m.p.: 110–111° C. |
| 60. | 3-methyl-N—(2-propoxyethyl)-carbanilic acid-(3-(methoxycarbonylamino)-phenyl)-ester | $n_D^{20}$: 1.5490 |
| 61. | N—(2-butoxyethyl)-4-methylcarbanilic acid-(3-(methoxycarbonylamino)-phenyl)-ester | $n_D^{20}$: 1.5427 |
| 62. | 3-methoxy-N—(2-methoxyethyl)-carbanilic acid-(3-methoxycarbonylamino)-phenyl)-ester | $n_D^{20}$: 1.5566 |
| 63. | N—(2-butoxyethyl)-carbanilic acid-(3-(methoxycarbonylamino)-phenyl)-ester | $n_D^{20}$: 1.5390 |
| 64. | 4-methyl-N—(2-propoxyethyl)-carbanilic acid-(3-(methoxycarbonylamino)-phenyl)-ester | m.p.: 62–63° C. |
| 65. | N—(2-methoxyethyl)-2-methylcarbanilic acid-(3-(ethoxycarbonylamino)-phenyl)-ester | m.p.: 98–100° C. |
| 66. | N—(2-methoxyethyl)-2-methylcarbanilic acid-(3-(ethylthiocarbonylamino)-phenyl)-ester | m.p.: 115–117° C. |
| 67. | N—(2-methoxyethyl)-3-methylcarbanilic acid-(3-(1-methylethoxycarbonylamino)-phenyl)-ester | m.p.: 93–94° C. |
| 68. | N—(2-methoxyethyl)-3-methylcarbanilic acid-(3-(2-propinyloxycarbonylamino)-phenyl)-ester | m.p.: 90–92° C. |
| 69. | N—(2-butoxyethyl)-carbanilic acid-(3-(ethoxycarbonylamino)-phenyl)-ester | $n_D^{20}$: 1.5340 |
| 70. | 3-methoxy-N—(2-methoxyethyl)-carbanilic acid-(3-(ethoxycarbonylamino)-phenyl)-ester | $n_D^{20}$: 1.5552 |
| 71. | N—(2-methoxyethyl)-3-methylcarbanilic acid-(3-(ethylthio-carbonylamino)-phenyl)-ester | $n_D^{20}$: 1.5716 |
| 72. | N—(2-methoxyethyl)-3-methylcarbanilic acid-(3-(2-methylpropoxycarbonylamino)-phenyl)-ester | $n_D^{20}$: 1.5439 |
| 73. | N—(2-ethoxyethyl)-carbanilic acid-(3-(2-methylpropoxycarbonylamino)-phenyl)-ester | $n_D^{20}$: 1.5354 |
| 74. | N—(2-ethoxyethyl)-3-methylcarbanilic acid-(3-(2-methylpropoxycarbonylamino)-phenyl)-ester | $n_D^{20}$: 1.5383 |
| 75. | N—(2-ethoxyethyl)-carbanilic acid-(3-(1-methylpropoxycarbonylamino)-phenyl)-ester | $n_D^{20}$: 1.5419 |
| 76. | N—(2-methoxyethyl)-carbanilic acid-(3-(1-methyl-2-chloroethoxycarbonylamino)-phenyl)-ester | m.p.: 109° C. |
| 77. | N—(2,2-dimethoxyethyl)-carbanilic acid-(3-(1-methyl-2-chloroethoxycarbonylamino)-phenyl)-ester | m.p.: 88–89° C. |
| 78. | N—(2,2-dimethoxyethyl)-carbanilic acid-(3-(2-bromoethoxycarbonylamino)-phenyl)-ester | $n_D^{20}$: 1.5528 |
| 79. | N—(2,2-dimethoxyethyl)-carbanilic acid-(3-(2-methoxyethoxycarbonylamino)-phenyl)-ester | $n_D^{20}$: 1.5379 |
| 80. | N—(2-methoxyethyl)-2-methylcarbanilic acid-(3-(methylthio-carbonylamino)-phenyl)-ester | m.p.: 110–112° C. |
| 81. | 3-methyl-N—(2-propoxyethyl)-carbanilic acid-(3-(2-methylpropoxycarbonylamino)-phenyl)-ester | $n_D^{20}$: 1.5374 |
| 82. | N—(2-methoxyethyl)-4-methylcarbanilic acid-(3-(2-methylpropoxycarbonylamino)-phenyl)-ester | $n_D^{20}$: 1.5456 |
| 83. | N—(2-methoxyethyl)-3-methylcarbanilic acid-(3-(2-methylpropoxycarbonylamino)-phenyl)-ester | m.p.: 74–75° C. |
| 84. | N—(2-methoxyethyl)-4-methylcarbanilic acid-(3-(methylthio-carbonylamino)-phenyl)-ester | m.p.: 107–109° C. |
| 85. | N—(2-ethoxyethyl)-3-methylcarbanilic acid-(3-(methylthio-carbonylamino)-phenyl)-ester | m.p.: 93–95° C. |
| 86. | N—(2-butoxyethyl)-4-methylcarbanilic acid-(3-(methylthio-carbonylamino)-phenyl)-ester | $n_D^{20}$: 1.5593 |
| 87. | N—(2-ethoxyethyl)-2-methylcarbanilic acid-(3-(methylthio-carbonylamino)-phenyl)-ester | $n_D^{20}$: 1.5786 |
| 88. | N—(2-ethoxyethyl)-carbanilic acid-(3-(methylthio-carbonylamino)-phenyl)-ester | m.p.: 82–84° C. |

-continued

| Compound No. | Name of Compound | Physical constants |
|---|---|---|
| | ester | |
| 89. | N—(2-methoxyethyl)-3-methoxycarbanilic acid-(3-(methylthio-carbonyl-amino)-phenyl)-ester | $n_D^{20}$: 1.5868 |
| 90. | N—(2-butoxyethyl)-carbanilic acid-(3-(methylthio-carbonylamino)-phenyl)-ester | $n_D^{20}$: 1.5550 |
| 91. | N—(2-methoxyethyl)-4-methoxycarbanilic acid-(3-(ethylthio-carbonyl-amino)-phenyl)-ester | $n_D^{20}$: 1.5727 |
| 92. | N—(2-methoxyethyl)-4-methoxycarbanilic acid-(3-(1-methylethoxycarbonyl-amino)-phenyl)-ester | $n_D^{20}$: 1.5482 |
| 93. | N—(2-methoxyethyl)-4-methoxycarbanilic acid-(3-(2-propinyloxycarbonyl-amino)-phenyl)-ester | $n_D^{20}$: 1.5597 |
| 94. | N—(2-methoxyethyl)-4-methoxycarbanilic acid-(3-(1-methylpropoxycarbonyl-amino)-phenyl)-ester | $n_D^{20}$: 1.5420 |
| 95. | N—(2-methoxyethyl)-4-methoxycarbanilic acid-(3-(2-methylpropoxycarbonyl-amino)-phenyl)-ester | $n_D^{20}$: 1.5483 |
| 96. | 3-methyl-N—(2-propoxyethyl)-carbanilic acid-(3-(methylthio-carbonylamino)-phenyl)-ester | m.p.: 74–75° C. |
| 97. | 4-methoxy-N—(2-methoxyethyl)-carbanilic acid-(3-(methylthiocarbonyl-amino)-phenyl)-ester | m.p.: 98–100° C. |
| 98. | N—(2,2-diethoxyethyl)-carbanilic acid-[3-(methoxycarbonylamino)-phenyl]-ester | m.p.: 82–83° C. |
| 99. | N—(2,2-diethoxyethyl)-carbanilic acid-[3-(ethylthio-carbonylamino)-phenyl]-ester | m.p.: 84° C. |
| 100. | N—(2-ethoxyethyl)-carbanilic acid-[3-(allyloxycarbonylamino)-phenyl]-ester | $n_D^{20}$: 1.5538 |
| 101. | N—(2-ethoxyethyl)-3-methylcarbanilic acid-[3-(allyloxycarbonyl-amino)-phenyl]-ester | $n_D^{20}$: 1.5533 |
| 102. | N—(2-propoxyethyl)-carbanilic acid-[3-(allyloxycarbonylamino)-phenyl]-ester | $n_D^{20}$: 1.5458 |
| 103. | N—(methoxyethyl)-carbanilic acid-[3-(2-bromoethoxycarbonylamino)-phenyl]-ester | $n_D^{20}$: 1.5574 |
| 104. | N—(2-butoxyethyl)-3-methylcarbanilic acid-[3-(methoxycarbonylamino)-phenyl]-ester | $n_D^{20}$: 1.5429 |
| 105. | N—(2-butoxyethyl)-3-methylcarbanilic acid-[3-(ethoxycarbonylamino)-phenyl]-ester | $n_D^{20}$: 1.5394 |
| 106. | N—(2,2-diethoxyethyl)-carbanilic acid-[3-(ethoxycarbonylamino)-phenyl]-ester | $n_D^{20}$: 1.7010 |
| 107. | N—(2-propoxyethyl)-carbanilic acid-[3-(1-methylethoxycarbonyl-amino)-phenyl]-ester | $n_D^{20}$: 1.5355 |
| 108. | N—(2-butoxyethyl)-3-methylcarbanilic acid-[3-(1-methylethoxycarbonyl-amino)-phenyl]-ester | $n_D^{20}$: 1.5345 |
| 109. | 3-methyl-N—(2-propoxyethyl)-carbanilic acid-[3-(1-methylethoxycarbonyl-amino)-phenyl]-ester | m.p.: 83–85° C. |
| 110. | N—(2-butoxyethyl)-4-methylcarbanilic acid-[3-(1-methylethoxycarbonyl-amino)-phenyl]-ester | $n_D^{20}$: 1.5241 |
| 111. | N—(2-butoxyethyl)-carbanilic acid-[3-(1-methylethoxycarbonylamino)-phenyl]-ester | $n_D^{20}$: 1.5289 |
| 112. | N—(2,2-diethoxyethyl)-carbanilic acid-[3-(allyloxycarbonylamino)-phenyl]-ester | $n_D^{20}$: 1.6388 |
| 113. | N—(2-methoxyethyl)-2-methylcarbanilic acid-[3-(2-propenyloxycarbonyl-amino)-phenyl]-ester | m.p.: 88–90° C. |
| 114. | N—(2,2-diethoxyethyl)-carbanilic acid-[3-(2-methylpropoxycarbonyl-amino)-phenyl]-ester | $n_D^{20}$: 1.6900 |
| 115. | N—(2,2-diethoxyethyl)-carbanilic acid-[3-(2-propinyloxycarbonyl-amino)-phenyl]-ester | $n_D^{20}$: 1.6873 |
| 116. | N—(2-ethoxyethyl)-4-methylcarbanilic acid-[3-(methylthiocarbonylamino)-phenyl]-ester | m.p.: 104–105° C. |
| 117. | N—(2,2-diethoxyethyl)-carbanilic acid-[3-(methylthio-carbonylamino)-phenyl]-ester | m.p.: 83° C. |
| 118. | 4-methyl-N—(2-propoxyethyl)-carbanilic acid-[3-(methylthio-carbonylamino)-phenyl]-ester | m.p.: 103–104° C. |
| 119. | 2-methyl-N—(2-propoxyethyl)-carbanilic acid-[3-(methylthio-carbonylamino)-phenyl]-ester | $n_D^{20}$: 1.5681 |
| 120. | N—(2-butoxyethyl)-3-methylcarbanilic acid-[3-(methylthio-carbonylamino)-phenyl]-ester | $n_D^{20}$: 1.5648 |
| 121. | N—(2-propoxyethyl)-carbanilic acid-[3-(ethylthio-carbonylamino)-phenyl]-ester | $n_D^{20}$: 1.5694 |
| 122. | 3-methyl-N—(2-propoxyethyl)-carbanilic acid-[3-(ethylthio-carbonylamino)-phenyl]-ester | $n_D^{20}$: 1.5683 |
| 123. | N—(2-butoxyethyl)-3-methylcarbanilic acid-[3-(ethylthio-carbonylamino)-phenyl]-ester | $n_D^{20}$: 1.5588 |
| 124. | N—(2-butoxyethyl)-4-methylcarbanilic acid-[3-ethylthio-carbonylamino)-phenyl]-ester | m.p.: 62–64° C. |
| 125. | N—(2-cyanoethyl)-3-chlorocarbanilic acid-(3-(allyloxycarbonylamino)-phenyl)-ester | $n_D^{20}$: 1.5605 |
| 126. | 3-methyl-N—(2-propoxyethyl)-carbanilic acid-(3-(2-propinyloxycarbonyl-amino)-phenyl)-ester | m.p.: 84–86° C. |
| 127. | N—(2-propoxyethyl)-carbanilic acid-(3-(2-propinyloxycarbonyl-amino)-phenyl)-ester | $n_D^{20}$: 1.5477 |
| 128. | N—(2-butoxyethyl)-4-methylcarbanilic acid-(3-(2-propinyloxycarbonyl-amino)-phenyl)-ester | $n_D^{20}$: 1.5472 |
| 129. | N—(2-butoxyethyl)-carbanilic acid-(3-(2-propinyloxycarbonyl-amino)-phenyl)-ester | $n_D^{20}$: 1.5418 |
| 130. | 2-methyl-N—(2-propoxyethyl)-carbanilic acid-(3-(2-propinyloxycarbonylamino)-phenyl)-ester | $n_D^{20}$: 1.5472 |
| 131. | N—(2-butoxyethyl)-3-methylcarbanilic acid-(3-(2-propinyloxycarbonyl-amino)-phenyl)-ester | $n_D^{20}$: 1.5451 |
| 132. | 4-methyl-N—(2-propoxyethyl)-carbanilic acid-(3-(2-propinyloxycarbonyl-amino)-phenyl)-ester | m.p.: 73–75° C. |
| 133. | N—(2-ethoxyethyl)-carbanilic acid-(3-(ethylthiocarbonylamino)-phenyl-ester | m.p.: 92–93° C. |
| 134. | N—(2-ethoxyethyl)-3-methylcarbanilic acid-(3-(ethylthiocarbonylamino)-phenyl)-ester | $n_D^{20}$: 1.5675 |
| 135. | 2-methyl-N—(2-propoxyethyl)-carbanilic acid-(3-ethylthiocarbonylamino)-phenyl)-ester | $n_D^{20}$: 1.5578 |
| 136. | N—(2-ethoxyethyl)-4-methylcarbanilic acid-(3-(ethylthiocarbonylamino)-phenyl)-ester | $n_D^{20}$: 1.5643 |
| 137. | 4-methyl-N—(2-propoxyethyl)-carbanilic acid-(3-(ethylthiocarbonylamino)-phenyl)-ester | m.p.: 72–74° C. |
| 138. | N—(2-methoxyethyl)-4-methylcarbanilic acid-(3-(ethylthiocarbonylamino)-phenyl)-ester | m.p.: 76–77° C. |
| 139. | N—(2-ethoxyethyl)-2-methylcarbanilic acid-(3-(ethylthiocarbonylamino)-phenyl)-ester | m.p.: 88–90° C. |
| 140. | N—(2-methoxyethyl)-3-methoxycarbanilic acid-(3-(ethylthio-carbonylamino)-phenyl)-ester | m.p.: 88–89° C. |
| 141. | N—(2-methoxyethyl)-3-methylcarbanil- | $n_D^{20}$: 1.5926 |

-continued

| Compound No. | Name of Compound | Physical constants |
|---|---|---|
| | ic acid-(3-(methylthio-carbonylamino)-phenyl)-ester | |
| 142. | 2-methyl-N—(2-propoxyethyl)-carbanilic acid-(3-(ethoxycarbonylamino)-phenyl)-ester | $n_D^{20}$: 1.5286 |
| 143. | N—(2-ethoxyethyl)-carbanilic acid-(3-(1-methylethoxycarbonylamino)-phenyl)-ester | $n_D^{20}$: 1.5400 |
| 144. | N—(2-methoxyethyl)-4-methylcarbanilic-(3-(1-methylethoxycarbonylamino)-phenyl)-ester | $n_D^{20}$: 1.5357 |
| 145. | N—(2-ethoxyethyl)-4-methylcarbanilic acid-(3-(1-methylethoxycarbonylamino)-phenyl)-ester | $n_D^{20}$: 1.5361 |
| 146. | 1-methyl-N—(2-propoxyethyl)-carbanilic acid-(3-(1-methylethoxycarbonylamino)-phenyl)-ester | $n_D^{20}$: 1.5328 |
| 147. | 4-methyl-N—(2-propoxyethyl)-carbanilic acid-(3-(1-methylethoxycarbonylamino)-phenyl)-ester | $n_D^{20}$: 1.5354 |
| 148. | 4-methyl-N—(2-propoxyethyl)-carbanilic acid-(3-(ethoxycarbonylamino)-phenyl)-ester | m.p.: 78–80° C. |
| 149. | N—(2-ethoxyethyl)-3-methylcarbanilic acid-(3-(1-methylethoxycarbonylamino)-phenyl)-ester | m.p.: 78–80° C. |
| 150. | N—(2-ethoxyethyl)-2-methylcarbanilic acid-(3-(1-methylethoxycarbonylamino)-phenyl)-ester | m.p.: 79–81° C. |

These compounds are soluble for instance in acetone, cyclohexanone, acetic acid ethylester, isophorone, tetrahydrofuran, dioxane, dimethylformamide and hexamethylphosphoric acid triamide. They are virtually insoluble in water and light gasoline.

The starting products for making the compounds of the invention according to the above processes are known or conventional.

The following examples will further illustrate the application and use of the compounds of the invention.

APPLICATION AND USES

EXAMPLE 2

The compounds of the invention listed in the following Table I were applied in a hothouse in amounts of 5 kg of active agent per about 2.5 acres and dissolved in 600 liters of water per about 2.5 acres to Sinapis and Solanum as test plants. The application was effected by spraying the plants. The results were evaluated three weeks after treatment on a scale from 0=no effect to 4=total destruction of the plants.

As appears from Table I normally a destruction of the test plants was accomplished.

TABLE I

| Compound of the Invention | Sinapis | Solanum |
|---|---|---|
| N—(2-methoxyethyl)-carbanilic acid-(3-(methoxycarbonylamino)-phenyl)-ester | 4 | 4 |
| N—(2,2-dimethoxyethyl)-carbanilic acid-(3-(methoxycarbonylamino)-phenyl)-ester | 4 | 4 |
| N—(2-methoxyethyl)-3-methylcarbanilic acid-(3-(methoxycarbonylamino)-phenyl)-ester | 4 | 4 |
| N—(2-methoxyethyl)-carbanilic acid-(3-(ethoxycarbonylamino)-phenyl)-ester | 4 | 4 |
| N—(2,2-dimethoxyethyl)-carbanilic acid-(3-isopropoxycarbonylamino)-phenyl)-ester | 4 | 4 |
| N—(2-methoxyethyl)-carbanilic acid-(3-(isopropoxycarbonylamino)-phenyl)-ester | 4 | 4 |
| N—(2-methoxyethyl)-carbanilic acid-(3-(sec.-butoxycarbonylamino)-phenyl)-ester | 4 | 4 |
| N—(2,2-dimethoxyethyl)-carbanilic acid-(3-(isobutylcarbonylamino)-phenyl)-ester | 4 | 4 |
| N—(2-methoxyethyl)-carbanilic acid-(3-(2-methylpropoxycarbonylamino)-phenyl)-ester | 4 | 4 |
| N—(2-methoxyethyl)-carbanilic acid-(3-(allyloxycarbonylamino)-phenyl)-ester | 4 | 4 |
| N—(2,2-dimethoxyethyl)-carbanilic acid-(3-(allyloxycarbonylamino)-phenyl)-ester | 4 | 4 |
| N—(2,2-dimethoxyethyl)-carbanilic acid-(3-(2-propinyloxycarbonylamino)-phenyl)-ester | 4 | 4 |
| N—(2-methoxyethyl)-carbanilic acid-(3-(2-propinyloxycarbonylamino)-phenyl)-ester | 4 | 4 |
| N—(2,2-dimethoxyethyl)-carbanilic acid-(3-(methylthiocarbonylamino)-phenyl)-ester | 4 | 4 |
| N—(2,2-dimethoxyethyl)-carbanilic acid-(3-(ethylthiocarbonylamino)-phenyl)-ester | 4 | 4 |
| N—(2-methoxyethyl)-carbanilic acid-(3-ethylthiocarbonylamino)-phenyl)-ester | 4 | 4 |
| N—(2-ethoxyethyl)-carbanilic acid-(3-methoxycarbonylamino)-phenyl)-ester | 4 | 4 |
| N—(2-ethoxyethyl)-3-methylcarbanilic acid-(3-(methoxycarbonylamino)-phenyl)-ester | 4 | 4 |
| N—(2,2-dimethoxyethyl)-3-methylcarbanilic acid-(3-(methoxycarbonylamino)-phenyl)-ester | 4 | 4 |
| N—(2,2-dimethoxyethyl)-4-methylcarbanilic acid-(3-(methoxycarbonylamino)-phenyl)-ester | 4 | 4 |
| N—(2-methoxyethyl)-3-methylcarbanilic-(3-(ethoxycarbonylamino)-phenyl)-ester | 4 | 4 |
| N—(2-ethoxyethyl)-carbanilic acid-(3-(ethoxycarbonylamino)-phenyl)-ester | 4 | 4 |
| N—(2,2-dimethoxyethyl)-3-methylcarbanilic acid-(3-(ethoxycarbonylamino)-phenyl)-ester | 4 | 4 |
| N—(2-ethoxyethyl)-3-methylcarbanilic acid-(3-ethoxycarbonylamino)-phenyl)-ester | 4 | 4 |
| N—(2,2-dimethoxyethyl)-4-methylcarbanilic acid-(3-ethoxycarbonylamino)-phenyl)-ester | 4 | 4 |
| N—(2,2-dimethoxyethyl)-4-methylcarbanilic acid-(3-(isopropoxycarbonylamino)-phenyl)-ester | 4 | 4 |
| N—(2,2-dimethoxyethyl)-3-methylcarbanilic acid-(3-(1-methylethoxycarbonylamino)-phenyl)-ester | 4 | 4 |
| N—(2,2-dimethoxyethyl)-4-methylcarbanilic acid-(3-butoxycarbonylamino)-phenyl)-ester | 4 | 4 |
| N—(2,2-dimethoxyethyl)-3-methcarbanilic acid-(3-(2-methylpropoxycarbonylamino)-phenyl)-ester | 4 | 4 |
| N—(2,2-dimethoxyethyl)-3-methylcarbanilic acid-(3-(1-methylpropoxycarbonylamino)-phenyl)-ester | 4 | 4 |
| N—(2,2-dimethoxyethyl)-4-methylcarbanilic acid-(3-(2-methylpropoxycarbonylamino)-phenyl)-ester | 4 | 4 |
| N—(2,2-dimethoxyethyl)-3-methylcarbanilic acid-(3-(2-methoxyethoxycarbonylamino)-phenyl)-ester | 4 | 4 |
| N—(2,2-dimethoxyethyl)-3-methylcarbanilic acid-(3-(allyloxycarbonylamino)-phenyl)-ester | 4 | 4 |
| N—(2,2-dimethoxyethyl)-3-methylcarbanilic acid-(3-(2-propinyloxycarbonylamino)-phenyl)-ester | 4 | 4 |
| N—(2,2-dimethoxyethyl)-4-methylcarbanilic acid-(3-(2-propinyloxycarbonylamino)-phenyl)-ester | 4 | 4 |
| N—(2-methoxyethyl)-carbanilic acid-(3-methylthiocarbonylamino)-phenyl)-ester | 4 | 4 |
| N—(2,2-dimethoxyethyl)-4-methylcarbanilic acid-(3-(methylthio-carbonylamino)-phenyl) | | |

TABLE I-continued

| Compound of the Invention | Sinapis | Solanum |
|---|---|---|
| ester | | |
| N—(2,2-dimethoxyethyl)-3-methylcarbanilic acid-(3-methylthiocarbonylamino)-phenyl-ester | 4 | 4 |
| N—(2,2-dimethyoxyethyl)-3-methylcarbanilic acid-(3-(ethylthiocarbonylamino)-phenyl)-ester | 4 | 4 |
| N—(2,2-dimethoxyethyl)-4-methylcarbanilic acid-(3-(ethylthiocarbonylamino)-phenyl)-ester | 4 | 4 |
| N—(2-ethoxyethyl)-3-methylcarbanilic acid-(3-(methylthio-carbonylamino)-phenyl)-ester | 4 | 4 |
| N—(2-methoxyethyl)-4-methylcarbanilic acid-(3-(methylthiocarbonylamino)-phenyl)-ester | 4 | 4 |
| N—(2-butoxyethyl)-4-methylcarbanilic acid-(3-(methylthio-carbonylamino)-phenyl)-ester | 4 | 4 |
| N—(2-ethoxyethyl)-2-methylcarbanilic acid-(3-(methylthio-carbonylamino)-phenyl)-ester | 4 | 4 |
| N—(2-methoxyethyl)-3-methoxycarbanilic acid-(3-(methylthio-carbonylamino)-phenyl)-ester | 4 | 4 |
| N—(2-butoxyethyl)-carbanilic acid-(3-methyl-thiocarbonylamino)-phenyl)-ester | 4 | 4 |
| N—(2-methoxyethyl)-4-methoxycarbanilic acid-(3-(ethylthiocarbonylamino)-phenyl)-ester | 3 | 3 |
| N—(2-methoxyethyl)-4-methoxycarbanilic acid-(3-(1-methylethoxycarbonylamino)-phenyl)-ester | 4 | 4 |
| N—(2-ethoxyethyl)-carbanilic acid-(3-(methyl-thio-carbonylamino)-phenyl-ester | 4 | 4 |
| N—(2-methoxyethyl)-4-methoxycarbanilic acid-(3-(2-propinyloxycarbonylamino)-phenyl)-ester | 4 | 4 |
| N—(2-methoyethyl)-4-methoxycarbanilic acid-(3-(1-methylpropoxycarbonylamino)-phenyl)-ester | 4 | 4 |
| N—(2-methoxyethyl)-4-methoxycarbanilic acid-(3-(2-methylpropoxycarbonylamino)-phenyl)-ester | 4 | 4 |
| N—(2-methoxyethyl)-3-methylcarbanilic acid-(3-(ethylthiocarbonylamino)-phenyl)-ester | 3 | 3 |
| N—(2-methoxyethyl)-3-methylcarbanilic acid-(3-(2-methylpropoxycarbonylamino)-phenyl)-ester | 4 | 4 |
| N—(2-ethoxyethyl)-carbanilic acid-(3-(2-methylpropoxycarbonylamino)-phenyl)-ester | 4 | 4 |
| N—(2-ethoxyethyl)-3-methylcarbanilic acid-(3-(2-methylpropoxycarbonylamino)-phenyl)-ester | 4 | 4 |
| N—(2-ethoxyethyl)-carbanilic acid-(3-(1-methylpropoxycarbonylamino)-phenyl)-ester | 4 | 4 |
| N—(2-methoxyethyl)-carbanilic acid-(3-(1-methyl-2-chloroethoxycarbonylamino)-phenyl)-ester | 2 | 2 |
| N—(2,2-dimethoxyethyl)-carbanilic acid-(3-(1-methyl-2-chloroethoxycarbonylamino)-phenyl)-ester | 2 | 2 |
| N—(2-methoxyethyl)-4-methoxycarbanilic acid-(3-(methylthiocarbonylamino)-phenyl)-ester | 4 | 4 |
| N—(2,2-dimethoxyethyl)-carbanilic acid-(3-(2-bromoethoxycarbonylamino)-phenyl)-ester | 3 | 2 |
| N—(2,2-dimethoxyethyl)-carbanilic acid-(3-(2-methoxyethoxycarbonylamino)-phenyl)-ester | 4 | 4 |
| N—(2-methoxyethyl)-2-methylcarbanilic acid-(3-(methylthiocarbonylamino)-phenyl)-ester | 4 | 4 |
| 3-methyl-N—(2-propoxyethyl)-carbanilic acid-(3-(2-methylpropoxycarbonylamino)-phenyl)-ester | 4 | 4 |
| N—(2-methoxyethyl)-4-methylcarbanilic acid-(3-(2-methylpropoxycarbonylamino)-phenyl)-ester | 4 | 4 |
| N—(2-methoxyethyl)-3-methylcarbanilic acid-(3-(1-methylpropoxycarbonylamino)-phenyl)-ester | 4 | 4 |
| 3-methyl-N—(2-propoxyethyl)-carbanilic acid-(3-methylthiocarbonylamino)-phenyl)-ester | 4 | 4 |
| N—(2-ethoxyethyl)-carbanilic acid-(3-(allyloxycarbonylamino)-phenyl)-ester | 4 | 4 |
| N—(2-ethoxyethyl)-3-methylcarbanilic acid-(3-(allyloxycarbonylamino)-phenyl)-ester | 4 | 4 |
| N—(2-propoxyethyl)-carbanilic acid-(3-(allyloxycarbonylamino)-phenyl)-ester | 4 | 4 |
| N—(methoxyethyl)-carbanilic acid-(3-(2-bromoethoxycarbonylamino)-phenyl)-ester | — | — |
| N—(2-butoxyethyl)-3-methylcarbanilic acid-(3-(methoxycarbonylamino)-phenyl)-ester | 4 | 4 |
| N—(2-butoxyethyl)-3-methylcarbanilic acid-(3-(ethoxycarbonylamino)-phenyl)-ester | 4 | 4 |
| N—(2,2-diethoxyethyl)-carbanilic acid-(3-(ethoxycarbonylamino)-phenyl)-ester | 4 | 4 |
| N—(2-propoxyethyl)-carbanilic acid-(3-(1-methylethoxycarbonylamino)-phenyl)-ester | 4 | 4 |
| N—(2-butoxyethyl)-3-methylcarbanilic acid-(3-(1-methylethoxycarbonylamino)-phenyl)-ester | 4 | 4 |
| 3-methyl-N—(2-propoxyethyl)-carbanilic acid-(3-(1-methylethoxycarbonylamino)-phenyl)-ester | 4 | 4 |
| N—(2-butoxyethyl)-4-methylcarbanilic acid-(3-(1-methylethoxycarbonylamino)-phenyl)-ester | 4 | 4 |
| N—(2-butoxyethyl)-carbanilic acid-(3-(1-methylethoxycarbonylamino)-phenyl)-ester | 4 | 4 |
| N—(2,2-diethoxyethyl)-carbanilic acid-(3-(allyloxycarbonylamino)-phenyl)-ester | 4 | 4 |
| N—(2-methoxyethyl)-2-methylcarbanilic acid-(3-(2-propenyloxycarbonylamino)-phenyl)-ester | 4 | 4 |
| N—(2,2-diethoxyethyl)-carbanilic acid-(3-(2-methylpropoxycarbonylamino)-phenyl)-ester | 4 | 4 |
| N—(2,2-diethoxyethyl)-carbanilic acid-(3-(2-propinyloxycarbonylamino)-phenyl-ester | 4 | 4 |
| N—(2-ethoxyethyl)-4-methylcarbanilic acid-(3-(methylthiocarbonylamino)-phenyl)-ester | 4 | 4 |
| N—(2,2-diethoxyethyl)-carbanilic acid-(3-(methylthio-carbonylamino)-phenyl)-ester | 4 | 4 |
| 4-methyl-N—(2-propoxyethyl)-carbanilic acid-(3-(methylthio-carbonylamino)-phenyl)-ester | 4 | 4 |
| 2-methyl-N—(2-propoxyethyl)-carbanilic acid-(3-(methylthio-carbonylamino)-phenyl)-ester | 4 | 4 |
| N—(2-butoxyethyl)-3-methylcarbanilic acid-(3-(methylthio-carbonylamino)-phenyl)-ester | 4 | 4 |
| N—(2-propoxyethyl)-carbanilic acid-(3-(ethylthio-carbonylamino)-phenyl)-ester | 4 | 4 |
| 3-methyl-N—(2-propoxyethyl)-carbanilic acid-(3-(ethylthio-carbonylamino)-phenyl)-ester | 4 | 4 |
| N—(2-butoxyethyl)-3-methylcarbanilic acid-(3-(ethylthio-carbonylamino)-phenyl)-ester | 4 | 4 |
| N—(2-butoxyethyl)-4-methylcarbanilic acid-(3-ethylthio-carbonylamino)-phenyl)-ester | 4 | 4 |
| N—(2-cyanoethyl)-3-chlorocarbanilic acid-(3-(allyloxycarbonylamino)-phenyl)-ester | 4 | 4 |
| 3-methyl-N—(2-propoxyethyl)-carbanilic acid-(3-(2-propinyloxycarbonylamino)-phenyl)-ester | 4 | 4 |
| N—(2-propoxyethyl)-carbanilic acid-(3-(2-propinyloxycarbonylamino)-phenyl)-ester | 4 | 4 |
| N—(2-butoxyethyl)-4-methylcarbanilic acid-(3-(2-propinyloxycarbonylamino)-phenyl)-ester | 4 | 4 |
| N—(2-butoxyethyl)-carbanilic acid-(3-(2-propinyloxycarbonylamino)-phenyl)-ester | 4 | 4 |
| 2-methyl-N—(2-propoxyethyl)-carbanilic acid-(3-(2-propinyloxycarbonylamino)-phenyl)-ester | 4 | 4 |
| N—(2-butoxyethyl)-3-methylcarbanilic acid-(3-(2-propinyloxycarbonylamino)-phenyl)-ester | 4 | 4 |
| 4-methyl-N—13 (2-propoxyethyl)-carbanilic acid-(3-(2-propinyloxycarbonylamino)-phenyl)-ester | 4 | 4 |
| N—(2-ethoxyethyl)-carbanilic acid-(3-(ethyl-thiocarbonylamino)-phenyl)-ester | 4 | 4 |
| N—(2-ethoxyethyl)-3-methylcarbanilic acid- | 4 | 4 |

TABLE I-continued

| Compound of the Invention | Sinapis | Solanum |
|---|---|---|
| (3-(ethylthiocarbonylamino)-phenyl)-ester | | |
| 2-methyl-N—(2-propoxyethyl)-carbanilic acid-(3-(ethylthiocarbonylamino)-phenyl)-ester | 4 | 4 |
| N—(2-ethoxyethyl)-4-methylcarbanilic acid-(3-(ethylthiocarbonylamino)-phenyl)-ester | 4 | 4 |
| 4-methyl-N-(2-propoxyethyl)-carbanilic acid-(3-(ethylthiocarbonylamino)-phenyl)-ester | 4 | 4 |
| N—(2-methoxyethyl)-4-methylcarbanilic acid-(3-ethylthiocarbonylamino)-phenyl)-ester | 4 | 4 |
| N—(2-ethoxyethyl)-2-methylcarbanilic acid-(3-(ethylthiocarbonylamino)-phenyl)-ester | 4 | 4 |
| N—(2-methoxyethyl)-3-methoxycarbanilic acid-(3-ethylthio-carbonylamino)-phenyl)-ester | 4 | 4 |
| N—(2-methoxyethyl)-3-methylcarbanilic acid-(3-(methylthio-carbonylamino)-phenyl)-ester | 4 | 4 |
| 2-methyl-N—(2-propoxyethyl)-carbanilic acid-(3-(ethoxycarbonylamino)-phenyl)-ester | 4 | 4 |
| N—(2-ethoxyethyl)-carbanilic acid-(3-(1-methylethoxycarbonylamino)-phenyl)-ester | 4 | 4 |
| N—(2-methoxyethyl)-4-methylcarbanilic acid-(3-(1-methylethoxycarbonylamino)-phenyl)-ester | 4 | 4 |
| N—(2-ethoxyethyl)-4-methylcarbanilic acid-(3-(1-methylethoxycarbonylamino)-phenyl)-ester | 4 | 4 |
| 1-methyl-N—(2-propoxyethyl)-carbanilic acid-(3-(1-methylethoxycarbonylamino)-phenyl)-ester | 4 | 4 |
| 4-methyl-N—(2-propoxyethyl)-carbanilic acid-(3-(1-methylethoxycarbonylamino)-phenyl)-ester | 4 | 4 |
| 4-methyl-N—(2-propoxyethyl)-carbanilic acid-(3-(ethoxycarbonylamino)-phenyl)-ester | 4 | 4 |
| N—(2-ethoxyethyl)-3-methylcarbanilic acid-(3-(1-methylethoxycarbonylamino)-phenyl)-ester | 4 | 4 |
| N—(2-ethoxyethyl)-2-methylcarbanilic acid-(3-(1-methylethoxycarbonylamino)-phenyl)-ester | 4 | 4 |

EXAMPLE 3

The compounds listed below in Table II and identified by the numbers of the above list of compounds were applied in a hothouse in a postemergence application to the plants likewise listed in the table. The amounts were 1 kg of active agent per about 2.5 acres. The comparison compound in the tests was 3-methyl-carbanilic acid-(3-(methoxycarbonylamino)-phenyl)-ester.

The plants were in the growing stage. The applied amount of liquid corresponded about to 500 liter per 2.5 acres. The agents were applied in the form of emulsions.

The results were evaluated after 14 days on a scale of 10=no damage to the plants to 0=total destruction of the plants.

As appears from the table with the compounds of the invention there resulted a good compatibility for agricultural plants together with a high activity against weeds. The composition compound on the other hand caused substantial damage to the agricultural plants at a lower weed activity.

TABLE II

| Compound of the Invention No. | potatoes | cotton | peanuts | rice | carrots | Digitalis | Valerianella | Trifolium | Portulaca | Papaver | Kochia | Solanum |
|---|---|---|---|---|---|---|---|---|---|---|---|---|
| 2. | 10 | 10 | 10 | 10 | 10 | 0 | 0 | 0 | 0 | 0 | 0 | 0 |
| 15. | 10 | 10 | 10 | 10 | 10 | 0 | 0 | 0 | 0 | 0 | 0 | 0 |
| 37. | 10 | 10 | 10 | 10 | 10 | 0 | 0 | 0 | 0 | 0 | 0 | 0 |
| Comparison compound 3-Methylcarbanilic acid -(3-(methoxycarbenylamino)-phenyl)-ester | 5 | 2 | 7 | 4 | 2 | 2 | 0 | 1 | 0 | 1 | 2 | 3 |
| Untreated | 10 | 10 | 10 | 10 | 10 | 10 | 10 | 10 | 10 | 10 | 10 | 10 |

| Compound of the Invention No. | Escholtzia | Euphorbia | Brassica | Datura | Ipomea | Setaria | Agrostis | Alopecurus | Bromus | Echinochloa | Digitaria |
|---|---|---|---|---|---|---|---|---|---|---|---|
| 2. | 0 | 0 | 0 | 0 | 0 | 0 | 0 | 0 | 0 | 0 | 0 |
| 15. | 0 | 0 | 0 | 0 | 0 | 0 | 0 | 0 | 0 | 0 | 0 |
| 37. | 0 | 0 | 0 | 0 | 0 | 0 | 0 | 0 | 0 | 0 | 0 |
| Comparison compound 3-Methylcarbanilic acid -(3-(methoxycarbenylamino)-phenyl)-ester | 1 | 3 | 0 | 0 | 0 | 3 | 5 | 7 | 6 | 10 | 8 |
| Untreated | 10 | 10 | 10 | 10 | 10 | 10 | 10 | 10 | 10 | 10 | 10 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspect of this invention.

What is claimed as new and desired to be protected by Letters Patent is set forth in the appended claims:

1. Diurethane of the formula

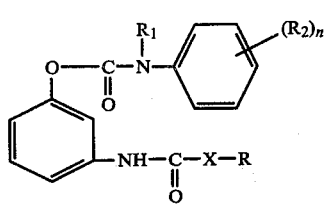

N-(2-Methoxyethyl)-carbanilic acid-(3-methoxy carbonylamino)-phenyl-ester, wherein $R=CH_3$, $X=O$, $R_1=$2-methoxyethyl and $n=0$.

2. Diurethane of the formula

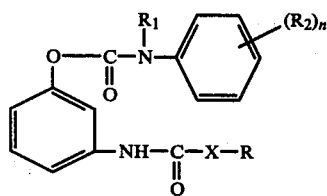

N-(2,2-Dimethoxyethyl)-carbanilic acid-(3-methylthiocarbonylamino)-phenyl-ester, wherein $R=CH_3$, $X=S$, $R_1=$2,2-dimethoxy ethyl and $n=o$.

3. Diurethane of the formula

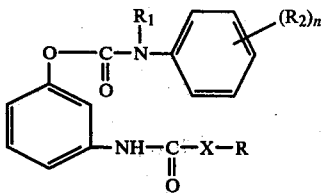

N-(2-Methoxyethyl)-carbanilic acid-(3-methylthiocarbonylamino)-phenyl-ester, wherein $R=CH_3$, $X=S$, $R_1=$2-methoxyethyl and $n=o$.

4. A herbicidal composition comprising from about 10 to 80% by weight of at least one diurethane selected from the group consisting of N-(2-Methoxyethyl)-carbanilic acid-(3-methoxy carbonylamino)-phenyl-ester, N-(2,2-Dimethoxyethyl)-carbanilic acid-(3-methylthiocarbonylamino)-phenyl-ester, and N-(2-Methoxyethyl)-carbanilic acid-(3-methylthiocarbonylamino)-phenyl-ester, and about 90 to 20% by weight of a liquid or solid inert carrier material with or without up to 20% by weight of a surface active agent upon corresponding reduction of the amount of carrier material.

* * * * *